United States Patent [19]

Biss et al.

[11] Patent Number: 5,077,047

[45] Date of Patent: Dec. 31, 1991

[54] PROCESS FOR PRODUCING PVP-$H_2O_2$ PRODUCTS IN THE FORM OF FREE-FLOWING POWDERS

[75] Inventors: Russell B. Biss, Paramus; Jeffrey Cohen, Fanwood; John J. Merianos, Middletown; Paul D. Taylor, West Milford, all of N.J.

[73] Assignee: ISP Investments Inc., Wilmington, Del.

[21] Appl. No.: 683,467

[22] Filed: Apr. 8, 1991

[51] Int. Cl.$^5$ ..................... A61K 31/79; A01N 25/00
[52] U.S. Cl. .................................... 525/387; 424/490; 424/405; 424/78.24; 427/213; 428/402
[58] Field of Search .................... 424/80, 490, 405; 427/213

[56] References Cited

U.S. PATENT DOCUMENTS

| | | | |
|---|---|---|---|
| 3,480,557 | 11/1969 | Shiraeff | 424/62 |
| 3,908,045 | 9/1975 | Alterman et al. | 427/213 |
| 4,655,786 | 4/1987 | Chun et al. | 427/213 |
| 5,008,106 | 4/1991 | Merianos et al. | 424/80 |
| 5,017,383 | 5/1991 | Ozawa et al. | 427/213 |

Primary Examiner—Thurman K. Page
Assistant Examiner—Amy Hulina
Attorney, Agent, or Firm—Walter Katz; Marilyn J. Maue; Joshua J. Ward

[57] ABSTRACT

A process for the production of PVP-$H_2O_2$ products in the form of free-flowing powders is described in which a fluidized bed maintained at a reaction temperature of about room temperature to 60° C. is contacted with finely divided droplets of a 30 to 85% by weight aqueous $H_2O_2$ solution. Preferably the fluidized bed temperature is about 35°-45° C., a 50-70% $H_2O_2$ solution is used, and the feed rate of introduction of the $H_2O_2$ solution is about 5-50 g/minute/kg PVP present. The PVP-$H_2O_2$ product preferably contains about 15-24%, preferably 18-22%, $H_2O_2$ (1:1 molar ratio) and less than about 5% water.

13 Claims, No Drawings 5,077,047

PROCESS FOR PRODUCING PVP-2O2 PRODUCTS IN THE FORM OF FREE-FLOWING POWDERS

FIELD OF THE INVENTION

This invention relates to a process for making a polyvinylpyrrolidone-hydrogen peroxide (PVP-$H_2O_2$) product, and more particularly, to a fluidized bed process for the production of such material in the form of free-flowing powders.

DESCRIPTION OF THE PRIOR ART

Stabilized $H_2O_2$ compositions have found wide utility in commercial and industrial applications, e.g. as antiseptics, disinfectants, sterilization agents, bleaching materials, washing concentrates, etchants, in cosmetic preparations, and as a catalyst in polymerizations requiring a free radical source. In biological applications which require an antiseptic, disinfectant or sterilization agent, such $H_2O_2$ compositions require release of an effective amount of oxygen at a desired rate.

Shiraeff, in U.S. Pat. Nos. 3,376,110 and 3,480,557, disclosed that a solid, stabilized hydrogen peroxide composition of hydrogen peroxide and a polymeric N-vinyl heterocyclic compound could be prepared from an aqueous solution of the components. The process involved mixing PVP and a substantial excess of aqueous $H_2O_2$ and evaporating the solution to dryness. The $H_2O_2$ content of the composition was given as being at least 2%, and preferably 4.5 to 70% by weight. Prolonged drying of the composition, in an attempt to reduce the water content, however, resulted in a substantial loss of $H_2O_2$ from the complex. The product was a brittle, transparent, gummy, amorphous material, and had a variable $H_2O_2$ content ranging from about 3.20 to 18.07% by weight, depending upon the drying times.

The Shiraeff process did not attain commercial success because (1) the product was not a free-flowing powder and thus could not be handled easily; (2) its water and hydrogen peroxide content varied over a wide range; (3) the complex was not stable; and (4) the aqueous process could not be carried out on a commercial scale.

Merianos, in copending U.S. patent application, Ser. No. 434,943, filed Nov. 8, 1989, described an improved process for making free-flowing, substantially anhydrous complexes of PVP and $H_2O_2$ by reacting PVP and a solution of $H_2O_2$ in an anhydrous organic solvent such as ethyl acetate. However, this process required the use of substantially anhydrous $H_2O_2$, which was too dangerous to handle industrially.

Rossberger et al., in German Patent OLS 3,444,552, published June 12, 1986, described a process for making urea peroxyhydrate using a fluidized bed of urea having a particle size of less than 1000$\mu$m onto which was sprayed an aqueous solution of concentrated $H_2O_2$. This technique was practical only because urea is a stable, crystalline compound which readily formed a free-flowing powdery complex upon addition of aqueous hydrogen peroxide solutions.

Production of free-flowing complexes of PVP-$H_2O_2$ from amorphous, polymeric, polyvinyl-pyrrolidone and aqueous $H_2O_2$, however, has not been easy to achieve commercially because, during production, the PVP polymer can alter its physical state, and/or retain excess water and/or free $H_2O_2$, even at elevated drying temperatures, resulting in a gummy rather than a free-flowing product.

Accordingly, it is an object of the present invention to provide a commercial process for the production of PVP-$H_2O_2$ products in the form of free-flowing powders.

Another object of the invention is to provide a fluidized bed process for making PVP-$H_2O_2$ products which are free-flowing by contacting a fluidized bed of PVP powders with a concentrated aqueous $H_2O_2$ solution under process conditions which favor formation of a free-flowing complex having about 15 to 24% by weight $H_2O_2$, preferably 18-22%, (1:1 molar ratio) without affecting the physical state of the PVP powders, and simultaneously and/or subsequently removing water from the product.

SUMMARY OF THE INVENTION

These and other objects and features of the invention are accomplished herein by providing a process for the production of PVP-$H_2O_2$ products in the form of free-flowing powders in which a fluidized bed of PVP powders maintained at a reaction temperature of from about ambient temperature to 60° C. is contacted with finely divided droplets of a 30 to 85% by weight aqueous $H_2O_2$ solution.

In the preferred embodiments of the invention, the bed temperature is maintained at about ambient temperature to 60° C., preferably 35°-45° C., a 50 to 70% aqueous $H_2O_2$ solution is used, and the feed rate for introduction of the $H_2O_2$ solution is about 5-50 g/minute/kg PVP used, preferably 15-25 g/minute/kg PVP.

The PVP-$H_2O_2$ product obtained herein is a free-flowing powder having about 15 to 24% by weight, preferably about 18-22%, $H_2O_2$ therein, which corresponds to a 1:1 molar ratio of its components, with no excess or free peroxide therein, and having less than about 5% water, which is about the same amount of water originally present in the PVP.

DETAILED DESCRIPTION OF THE INVENTION

In accordance with the present invention, a fluidized bed containing a charge of PVP powders is reacted with an aqueous solution of concentrated hydrogen peroxide. The PVP polymer can be obtained from GAF Chemicals Corporation in the form of a water-soluble or water-insoluble polymer, which has a molecular weight ranging from the K-15 to K-90 designations. These PVP polymers, which generally have a water content of about 5% by weight, or less, and a particle size of about 10 to 100 microns, may be used directly in the process of the invention, or pre-dried, if desired, to reduce its moisture content.

The hydrogen peroxide solution used herein usually contains about 30 to 85% hydrogen peroxide. A 50 to 70% $H_2O_2$ solution, however, is preferred because of the inherent danger present in use of the higher $H_2O_2$ concentrations.

The fluidized bed of PVP powders can be maintained in the fluidized condition by directing a current of dry air through the powders, by mechanical agitation of the powders, or by a combination of both techniques.

The fluidized bed is maintained at a suitable bed (reaction) temperature at which formation of the desired PVP-$H_2O_2$ complex product can occur readily without affecting the powdery state of the PVP polymer, and at which excess water from the $H_2O_2$ solution can be quickly removed both from the product and the PVP bed itself. The selected bed temperature also will enhance the formation of a free-flowing powder rather than a gum. Such suitable reaction temperatures range from about ambient temperature to 60° C., preferably about 35° to 45° C.

The aqueous concentrated $H_2O_2$ solution preferably is contacted with the PVP powders as finely divided droplets of liquid. Such desired droplets may be formed by pumping the $H_2O_2$ solution through a spray nozzle and onto the PVP bed at a selected rate and for a predetermined period of time. Any spray nozzle capable of producing a fine dispersion of droplets may be used for this purpose. If necessary, however, a stream of air may be introduced into such nozzle with the solution to assist in atomizing the solution into finely divided droplets.

The spray solution of aqueous $H_2O_2$ thus formed preferably is introduced into the fluidized bed of PVP powders at a selected rate such that excess water can be removed therein during formation of the complex without retaining free $H_2O_2$ therein. A suitable feed rate for introduction of the $H_2O_2$ solution is about 5-50 g/minute/kg PVP, preferably about 5-25 g/minute/kg PVP. Under these flow rate conditions, a free-flowing powder of the desired PVP-$H_2O_2$ complex is obtained containing about 15-24% $H_2O_2$, preferably 18-22%, and about 5% or less water therein.

In the preferred form of the process of the invention, the spray solution of $H_2O_2$ is directed onto the PVP bed for a period sufficient to form a free-flowing powder having an $H_2O_2$ content of about 15 to 24% by weight, preferably 18-22%, which is indicative of a complex having a 1:1 molar ratio of PVP to $H_2O_2$. At this point in the process, the feed is discontinued to preclude excess water and/or free $H_2O_2$ from forming on the free-flowing powder which can cause it to become gummy. The appearance of a gummy product is indicative of the presence of excess water and/or free $H_2O_2$ in the product.

The spray solution of $H_2O_2$ may be directed onto the fluidized bed as a vertical, horizontal or by downward flow of droplets.

If a fluidizing air stream is used to create the fluid bed, it is usually directed upwardly against the PVP powders. Such air currents also can assist in carrying water away from the bed. The fluidized state of the bed also may be maintained using mechanical agitation, or a combination of both air and mechanical means.

The process of the invention can be carried out in one or two steps, i.e. removal of water from the product and bed can take place either (a) simultaneous with or after mixing of the reaction components in the same apparatus, or (b) in a downstream drying step, or (c) by a combination of both steps. The particular method of drying will depend upon the type of equipment used. For example, if a fluidized bed mixer is used, such as a plowshare, belt screw or paddle mixer, then the moist PVP-$H_2O_2$ product can be dried further in a separate dryer. This sequence is characterized as a two-step process. Any suitable dryer can be used for this purpose, such as a vacuum, radiant heat or contact dryer.

Furthermore, if desired, application of the spray $H_2O_2$ solution onto the PVP bed, followed by downstream drying, may be carried out in several stages in order to increase the $H_2O_2$ content of the product towards the desired 1:1 molar ratio, and to reduce its water content.

Moreover, a fluid bed dryer may be used in the process which has the dual capabilities of providing both the fluidized bed and drying functions. Accordingly, drying of the product will begin and be completed during reaction between the PVP charge and the aqueous $H_2O_2$ solution. Such a process may be considered as taking place in a one-step.

Preferably, reaction and dehydration are continued until the product reaches a desired $H_2O_2$ content, suitably about 15-24% $H_2O_2$, and usually about 18-22%, with less than about 5% water, generally about 1-3%. However, it is essential that the product remain in the free-flowing state after completion of addition of the $H_2O_2$ solution.

The size of the fluidized bed reactor, the rate of addition of the hydrogen peroxide solution, and the reaction times will vary with the particular equipment used, as well as the concentration of the hydrogen peroxide solution and the reaction temperature, keeping in mind the purposes intended to be achieved with respect to each of these process parameters. However, it is believed that the following examples will illustrate the employment of these parameters to provide a process which can be used for the commercial production of the desired PVP-$H_2O_2$ products. These examples, of course, are given by way of illustration only, and are not to be construed as limiting the invention.

EXAMPLE 1

Production of PVP-$H_2O_2$ Product Using A Fluidized Bed Reactor and Vacuum Drying 0.35 kg of polyvinylpyrrolidone (PVP K-30, CI grade) having particle sizes of predominately 40-50 microns, and a moisture content of 2-3%, was introduced into a 0.4 l fluid bed reactor. The PVP powders were fluidized by passing a stream of dry air upwardly through the charge. The bed temperature was set at 35°-45° C. Then an aqueous solution of 70% $H_2O_2$ was metered through a spray nozzle with the assistance of an air stream and directed vertically onto the bed. The rate of addition of the solution was 15-25 g of solution/minute/kg PVP for 20 minutes. Adsorption of the solution onto the bed produced a wet product containing 18% $H_2O_2$ and 6% water. Subsequent downstream vacuum drying of the wet material at 25°-35° C. for 10 hours produced a free-flowing powder which had a 20-22% $H_2O_2$ content and only 3% water therein.

EXAMPLE 2

PVP-$H_2O_2$ Product Using Fluidized Bed Dryer 3.6 kg of polyvinylpyrrolidone (PVP K-30, CI grade), having a particle size of 40-50 microns, was packed into a 22 liter fluidized bed dryer and fluidized at 35°-45° C. using a dry air stream. Then a 70% $H_2O_2$ solution was introduced during 20 minutes at a feed rate of 10-15 g/minute/kg PVP. During the addition, water was being removed continuously from the product and the bed. Following completion of the $H_2O_2$ addition, the resultant product was dried further for 10 minutes. The resultant product was a free-flowing powdery complex of PVP-$H_2O_2$ having a peroxide content of 20% and a moisture content of only 2%.

EXAMPLE 3

PVP-$H_2O_2$ Product Using 30% $H_2O_2$

The procedure of Example 1 was followed using a 30% $H_2O_2$ solution at a feed rate of 20 g/minute/kg PVP for 20 minutes. Successive additions of $H_2O_2$ were followed by vacuum drying. After three stages of application and drying, the free-flowing product contained 19% $H_2O_2$ and 3% water.

EXAMPLE 4

One-Stage Production of PVP-$H_2O_2$ Product

The procedure of Example 2 was followed using a 50% $H_2O_2$ solution introduced at a feed rate of 15-22 g/minute/kg PVP. A free-flowing powder product was obtained after addition of the $H_2O_2$ solution into the fluidized bed dryer. The product contained 18-20% $H_2O_2$ and 3% water.

EXAMPLE 5

PVP-$H_2O_2$ From PVP K-90

The procedure of Example 1 was followed using PVP K-90 having a particle size of about 25-75 microns. The free-flowing product contained 17-20% $H_2O_2$ and 3% water.

EXAMPLE 6

PVP-$H_2O_2$ From PVP Crospovidone

The procedure of Example 1 was followed using crosslinked PVP (Crospovidone), which is a water-insoluble PVP, having a particle size of 10-25 microns, with 70% $H_2O_2$, at a feed rate of 30 g/minute/kg PVP. The free-flowing product contained 18% $H_2O_2$ and 3% water.

EXAMPLE 7

PVP-$H_2O_2$ From PVP Crospovidone Using Fluid Bed Dryer

The procedure of Example 6 was followed using a fluid bed dryer, at a $H_2O_2$ solution feed rate of 13 g/minute/kg PVP. The product contained 18% $H_2O_2$ and 2% water.

EXAMPLE 8

PVP-$H_2O_2$ From PVP K-15

The procedure of Example 1 was followed using PVP K-15 having a particle size of 50-80 microns. Two stages of addition and vacuum drying were required to produce a free-flowing product with a 15% $H_2O_2$ and 2% water content.

While the invention has been described with particular reference to certain embodiments thereof, it will be understood that changes and modifications may be made which are within the skill of the art. Accordingly, it is intended to be bound only by the following claims, in which

What is claimed is:

1. A process for the production of free-flowing powders of PVP-$H_2O_2$ comprising reacting a fluidized bed of PVP polymer maintained at a reaction temperature of from ambient temperature to about 60° C. with finely divided droplets of a 30 to 85% by weight aqueous solution of $H_2O_2$, wherein said $H_2O_2$ solution feed rate is about 5-50 g/minute/kg PVP and drying the product.

2. A process according to claim 1 wherein introduction of said solution is continued until the resultant product contains about 15 to 24% by weight $H_2O_2$.

3. A process according to claim 1 wherein said reaction temperature is about 35° to 45° C.

4. A process according to claim 1 wherein a 50 to 70% $H_2O_2$ solution is used.

5. A process according to claim 4 wherein said solution feed rate is about 15-25 g/minute/kg PVP.

6. A process according to claim 1 wherein drying is carried out in the fluidized bed during formation of the product, or in a downstream dryer.

7. A process according to claim 6 wherein both said reaction and drying steps are carried out in a fluidized bed dryer.

8. A process according to claim 6 wherein the reaction is carried out in a fluidized bed reactor, and further drying of the wet product is performed in a downstream dryer.

9. A process according to claim 1 wherein air is used to fluidize the PVP powders and to assist in removing water from the fluidized bed during the process.

10. A process according to claim 1 wherein the PVP powders are selected from water-soluble and water-insoluble PVP powders in a range of molecular weights corresponding to the designation K-15 to K-90 in a range of molecular weights corresponding to the designations K-15 to K-90.

11. A process according to claim 1 wherein the product contains about 5% or less water therein.

12. A process according to claim 10 wherein said PVP has a particle size of about 10-100 microns.

13. A process according to claim 1 wherein air is used to assist in forming spray droplets of the $H_2O_2$ solution.

* * * * *